United States Patent
Durham

[11] Patent Number: 6,086,596
[45] Date of Patent: Jul. 11, 2000

[54] MAGNETICALLY ASSISTED SURGICAL WIRING AND CABLING PASSER DEVICES

[76] Inventor: Alfred A. Durham, 2954 Lockrdge Rd., Roanoke, Va. 24014

[21] Appl. No.: 09/295,446

[22] Filed: Apr. 21, 1999

[51] Int. Cl.[7] .................................................. A61B 17/58
[52] U.S. Cl. .......................................................... 606/103
[58] Field of Search ............................. 606/103, 74, 215, 606/216, 72, 139

[56] References Cited

U.S. PATENT DOCUMENTS

| | | | |
|---|---|---|---|
| 1,641,077 | 8/1927 | Fouquet | 606/103 |
| 4,312,337 | 1/1982 | Donohue | 606/103 |
| 5,851,209 | 12/1998 | Kummer et al. | 606/103 |

*Primary Examiner*—Michael Buiz
*Assistant Examiner*—(Jackie) Tan-Uyen T. Ho
*Attorney, Agent, or Firm*—Larson & Taylor, PLC

[57] ABSTRACT

A surgical passer device is provided for passing a wire or cable around or along a bone of a patient. The passer device comprises two separate passer members which are curved such that, when they are joined, they fit around the bone. In one embodiment, both curved members are cannulated and include permanent magnets at the distal ends thereof which, when magnetically engaged, bring the cannulated members into alignment so that a cable or wire can be passed therethrough. The members are then withdrawn, leaving the cable around the bone. In a further embodiment, a cable with a tip magnet is loaded into a curved cannulated passer member with the magnet exposed and a further curved passer member is used to capture the tip magnet and pull it around the bone. In one implementation, the further member is a malleable rod that can be bent into a suitable curved shape.

23 Claims, 2 Drawing Sheets

MAGNETICALLY ASSISTED SURGICAL WIRING AND CABLING PASSER DEVICES

FIELD OF THE INVENTION

The present invention relates to the use of wires and cables in orthopedic surgery and, more particularly, to improved passer devices for surgical wiring and cabling employing magnetic assistance in the passing or placement of the wires and cables.

BACKGROUND OF THE INVENTION

Cables and twisted wires are used in orthopedic surgery to assist in the reattachment of major muscle groups, in the reconstruction of fractures such as those of the patella, and to safely wire fractures such as those of the femur when these fractures have occurred around implants. One of the difficult steps involved in the use of such cables and wires is that of passing them, in a safe manner, around the bone without entrapping vital soft tissue structures such as arteries and nerves.

In general, wires are usually pulled through soft tissue using a curved clamp. Typically, a cable passer device in the form of a curved tube is used to pass cables around the bone. Such a cable passer device is indicated at 10 in FIG. 1. As illustrated, the device 10 includes a curved tubular portion 10a which extends through about 270° of a circle, a cable entry portion 10b into which the cable is inserted for travel through the tubular portion 10a and a gripping handle 10c. A bone B is shown as being partially encircled by tubular portion 10a. Because the tubular portion 10 must be curved so as to extend over about 270° of arc, as shown, in order to permit the free end of the cable to be grabbed on the other side of the bone B from that at which the cable is inserted, a relatively large incision is required. Further, in order for the tubular portion 10a to pass all the way around the bone B, the circumference of tubular portion 10a must be much larger than the circumference of the bone. This large size can result in the unwanted capture or inclusion of vital structures under the passer 10.

SUMMARY OF THE INVENTION

In accordance with the invention, an improved device is provided for overcoming or reducing the problems associated with prior art methods and devices employing twisted wires or orthopedic cables to assist in restoring or augmenting fracture stability. These problems include, in particular, the basic problem described above, i.e., that, before use, the cables and wires must be passed through the soft tissues around the bone while avoiding the inclusion of nerves, blood vessels and other vital body structures and that prior art devices used for this purpose (curved clamps for pulling the wires through and curved tubes for passing the cables) are deficient in this regard.

According to the invention, a surgical passer device is provided which uses a magnet or magnets to assist the passing of cables and wires around bones and which is a substantial improvement over prior art cable and wire passer devices. As will appear, among other advantages thereof, the device of the invention is easy to use, rugged in construction, and less damaging to the vital soft tissue structures. In the latter regard, the curvature of the passer device of the invention can be made to accommodate the size of the bone, so that the passer device does less damage while passing the corresponding cable or wire more accurately.

According to one aspect of the invention, a surgical passer device is provided for passing a wire or cable around or along a bone of a patient, the passer device comprising: a first passer member including a first curved cannulated portion including a passage therethrough for receiving a wire or cable to be passed around the bone and having a curvature adapted to fit partially around the bone; and a second passer member including a second curved portion having a curvature adapted to fit partially around the bone such that when, in use of the device, the curved portions of the first and second passer members are brought into engagement with each other at the distal ends thereof, the passer device fits around the bone; the second passer member including a permanent magnet at the distal end of the second curved portion for facilitating passing around the bone of a wire or cable exiting from the passage in the cannulated portion of the first passer member.

In a first embodiment, the permanent magnet comprises a cannulated magnet and the second curved portion thereof includes a passage therethrough, and the first curved portion of the first passer member further includes a cannulated permanent magnet at the distal end thereof such that when the cannulated magnets of the first and second portions are magnetically engaged, a wire or cable can be passed around the bone through the passages in the first and second curved portions.

Preferably, in this embodiment, the first and second passer devices respectively comprise first and second handle portions including first and second further magnets, respectively, and first and second magnets are disposed in the handles so as to face each other so that when the further magnets are magnetically engaged, the first and second cannulated magnets are also magnetically engaged. Advantageously, the cannulated magnets have slanted distal surfaces to facilitate travel thereof through the soft tissues surrounding the bone.

In accordance with a further embodiment of this aspect of the invention, the wire or cable to be passed comprises a flexible elongate wire or cable element having a permanent distal magnet at the distal end thereof, and the permanent magnet at the distal end of the second curved portion includes means for engaging the distal permanent magnet so as to enable pulling of the flexible elongate element through the passage of the first passer member and around the bone. Preferably, the distal magnet has a non-flat shape and the magnet at the distal end of the second portion has a reciprocal non-flat shape. Advantageously, the distal magnet has a bullet shape and the magnet at the distal end of the second portion includes a recessed portion for receiving the distal magnet.

In a beneficial implementation, the distal end of the second portion includes at least one mechanical capture element. This mechanical capture element advantageously includes a scooped shape for facilitating passage thereof through soft tissue adjacent to the bone.

In a further implementation of this embodiment, the curved second portion of the second passer member comprises a malleable rod bendable to a desired curved shape by the user.

In yet another implementation of the embodiment, the first curved portion of the first passer member includes a permanent magnet, at the distal end thereof, of opposite polarity to that of the distal magnet of the flexible elongate element for repelling that distal magnet upon release of the flexible elongate element. This implementation is explained further below.

In accordance with a further aspect of the invention, a surgical passer device is provided for passing a wire or cable around or along a bone of a patient, said passer device comprising: first and second passer members, the first passer member including a first curved cannulated portion including a first passage therethrough for passing a wire or cable to the distal end thereof, and a first cannulated magnet at the distal end; and the second passer member including a second curved cannulated portion including a second passage therethrough for receiving a wire or cable passed from the first passer member and a second cannulated magnet, of opposite polarity to the first magnet, at the distal end thereof for, in operation of the device, magnetically engaging the first magnet when the first and second magnets are brought into proximity such that the first and second curved portions fit around a bone about which a wire or cable is to be passed, and so as to bring the first and second passages into alignment to thereby enable passing of a wire or cable around the bone through the first and second passages.

Preferably, the first and second passer devices respectively comprise first and second handle portions including first and second further magnets, respectively, and first and second magnets are disposed in the handles so as to face each other so that when the further magnets are magnetically engaged, the first and second cannulated magnets are also magnetically engaged.

Preferably, the first and second passer members are mirror images of one another. Advantageously, the curved portions are substantially C-shaped and, in use, face in opposite directions. The passage through the first curved portion of said first passer member preferably includes an inlet opening at a location between the proximal end of the passage and the distal end of the handle portion. Similarly, the passage through the second curved portion of the second passer member preferably includes an exit opening at a location between the proximal end of the passage and the distal end of the handle portion.

Advantageously, the cannulated magnets comprise neodymium magnets. In one embodiment, the cannulated magnets have flat distal surfaces. In a further embodiment, the cannulated magnets have slanted distal surfaces. Advantageously, the slanted distal surfaces are oppositely slanted at 450 so as to mate with one another.

According to yet another aspect of the invention, a surgical passer device is provided for passing a wire or cable around or along a bone of a patient, the passer device comprising: a flexible elongate wire or cable element including a distal permanent magnet at the distal end thereof; a first passer member including a first curved cannulated portion including a passage therethrough for receiving the flexible elongate element, with the distal magnet of the elongate element disposed at the distal end of the passage, and having a curvature adapted to fit partially around the bone; and a second passer member including a second curved portion having a curvature adapted to fit partially around the bone such that when, in use of the device, the curved first and second curved portions are brought into engagement with each other at the distal ends therein, the passer device fits around the bone; the second passer member including a permanent capture magnet at the distal end of the second curved portion thereof, in use of the passer device, magnetically engaging the distal magnet so as to enable pulling around the bone of the flexible elongate element through the passage in the cannulated portion of the first member. In one embodiment of this aspect of the invention, the curved second portion of the second passer member comprises a malleable rod bendable to a desired curved shape by the user.

Further features and advantages of the present invention will be set forth in, or apparent from, the detailed description of preferred embodiments thereof which follows.

DESCRIPTION OF THE PREFERRED EMBODIMENTS

Figure 1:
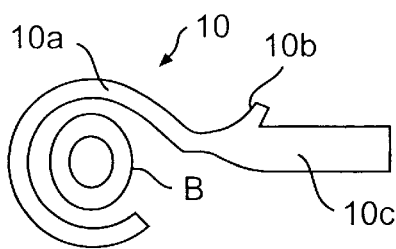
FIG. 1, which was described above, shows, in a schematic manner, a prior art passer device in use.
Figure 2:
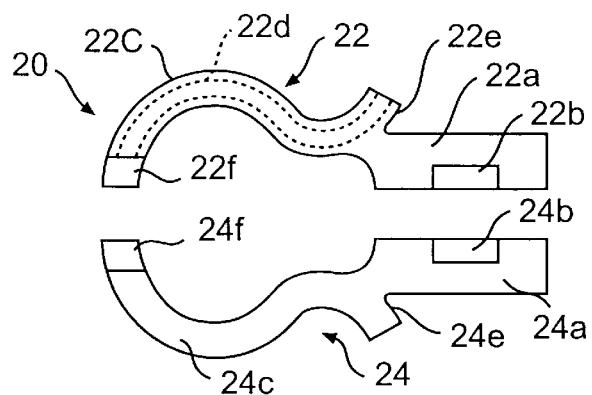
FIGS. 2 and 3 are side elevational views of a passer device in accordance with the first embodiment, with FIG. 3 showing the device in use with the passer members thereof in alignment.
Figure 3:
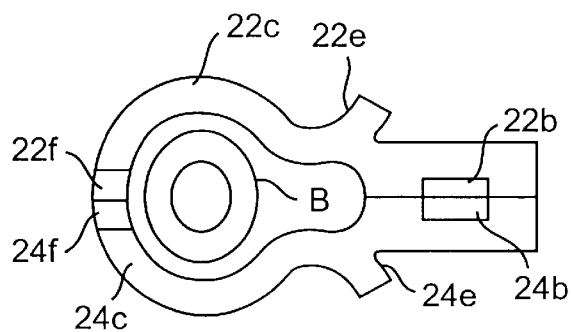

Referring to FIGS. 2 and 3, a first embodiment of the invention is shown. A passer device or passer, which is generally denoted 20, includes two separate members 22 and 24 which are the mirror images of each other and which are adapted to mate together as shown in FIG. 3. Because members 22 and 24 are essentially the same, reference in the following discussion will be made to member 22 as typical. Member 22 includes a handle portion 22a which includes a magnet 22b that, in the use of the device, faces a corresponding magnet 24b of the handle portion 24a of member 24. An integral hollow or cannulated arm portion or tubular portion 22c of member 24 is curved, generally in the shape of a "C", so as to fit around a bone B but only extends through about 180° of arc in contrast to the prior art passer device 10 of FIG. 1. A cannula or passage 22d in tubular portion 22c terminates at its proximal end in a cable entry port or inlet 22e. A second, cannulated magnet is located at the free or distal end of tubular portion 22c. The distal magnet 22f, and corresponding distal magnet 24f, are preferably strong magnets and most preferably neodymium magnets, and, in one embodiment, all of the magnets advantageously comprise neodymium magnets.

In use, the passer members 22 and 24 are inserted into an incision or incisions in the soft tissue on opposite sides of the bone B, and distal magnets 22f and 24f and proximal magnets 22b and 24b are used to bring the passer members 22 and 24 into alignment. In this regard, when the handle-mounted proximal magnets 22b and 24b are snapped together, this will also ensure that the distal magnets 22f and 24f are in engagement around the bone B, as shown in FIG. 3. A wire or cable (not shown) is then passed from one of the passer members, e.g. member 22, through the other, e.g., member 24, and pulled out through exit port 24e. After the cable is passed therethrough, the two passer members 22 and 24 are withdrawn from around the bone B and the cable remains around the bone.

Figure 5:
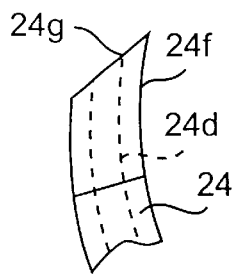
FIG. 5 is a view similar to FIG. 4 showing one of the magnets of FIG. 4.
Figure 4:
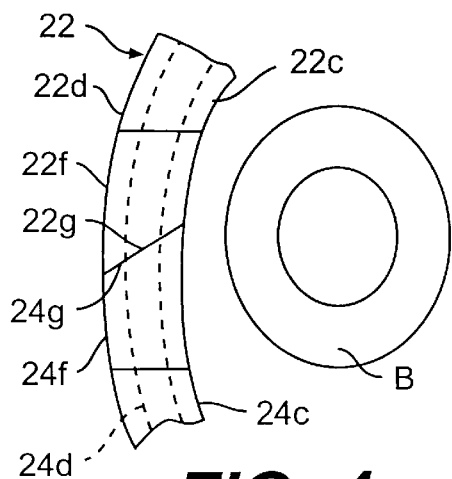
FIG. 4 is a side elevational view, partially broken away and drawn to an enlarged scale, of an alternative embodiment of the tip or distal magnets of FIGS. 2 and 3.

An alternative embodiment of this aspect of the invention is shown in FIGS. 4 and 5. In this embodiment, the magnets 22f and 24f at the tips of the tubular portions 22c and 24c are angled or slanted, i.e., provided with respective mating slant faces 22g and 24g. As is perhaps more evident from FIG. 4, which shows one of the magnets, the slanted tips 22g, 24g of magnets 22f, 24f help the tips pass through the soft tissue and are superior in this regard to square tips of FIGS. 2 and 3.

It is noted that the typical diameter of the cables for the tubular or cannulated portions is 1.6 to 2.0 mm and that the passers described above can be used with malleable or bendable wires in addition to cables.

Figure 6:
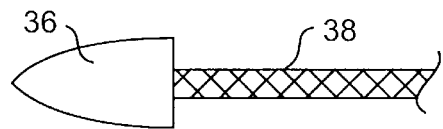
FIG. 6 is a side elevational view of a magnet tipped cable in accordance with a further preferred embodiment of the invention.
Figure 7:
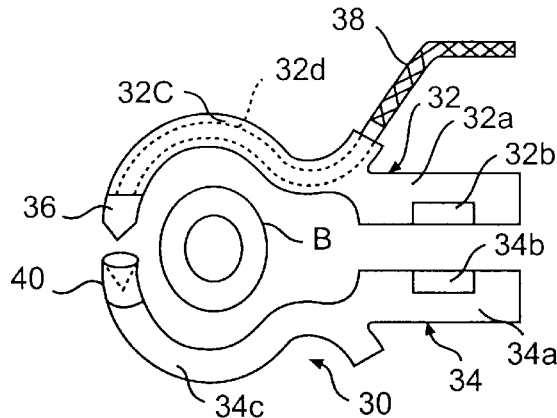
FIG. 7 is a side elevational view of a passer device in accordance with a further embodiment of the invention, including the cable of FIG. 6.

Referring to FIGS. 6 and 7, in accordance with a further aspect of the invention, a magnetic "assist" is provided using a passer device, generally denoted 30, wherein a magnet 36 is attached to the cable (or wire) 38 to be passed around the bone B. As shown in FIG. 6, the magnet 32 is preferably bullet shaped or is otherwise pointed or tapered. The passer device 30 illustrated in FIG. 7 is similar to passer device 20 and is formed in a similar manner by separate passer members 32 and 34. To simplify the description, like elements in FIG. 7 have been given the same letter suffixes as in FIGS. 2 and 3 so that, e.g., element 32a corresponds to element 22a, element 32b to element 22b, and so on. One difference is that the magnet at the tip of tubular portion 32 is eliminated and the cable 38 is passed through the passage 32d in tubular portion 32c from the distal end to the proximal end to thereby position the magnet 36 on cable 38 at the distal end of the tubular portion 32c. Further, the magnet at the tip end of tubular portion 34c of passer member 34 is preferably replaced by a magnetic capture element 40. Capture element 40 can simply screw into the free or distal end of the standard cannulated passer member 34. In the preferred embodiment illustrated, capture element 40 includes a generally conical recess which is adapted to receive, and capture, bullet shaped magnet 36. With magnet 36 so captured, by then withdrawing passer member 34, the cable 38 can be pulled through passer member 32 around the bone B.

It will, of course, be understood that the passer device of FIG. 7 can take other forms and that, for example, the passer member 34 need not include, because such is unnecessary, a passage and exit port corresponding to those of passer member 24 of FIGS. 2 and 3.

Figure 8:
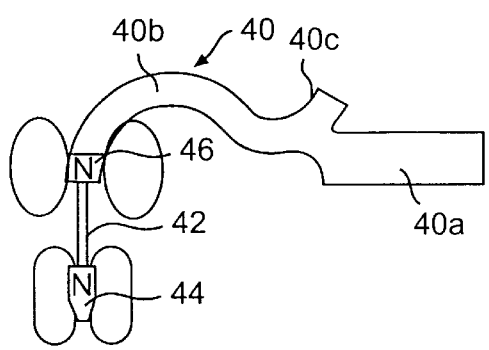
FIG. 8 is a side elevational view of a further embodiment of the invention.

Referring to FIG. 8, a further embodiment of the invention is illustrated. This embodiment is similar to FIG. 7 and comprises a passer member 40 including a handle 40a and a curved tubular portion 40b having an entry port 40c. A cable 42 with a bullet shaped magnet 44 is again fed into tubular or cannulated portion 40b from the distal end to the proximal end but, in this embodiment, a further magnet 46 is located at the distal end. Magnet 46 has an opposite polarity to that of magnet 44 so that, e.g., the North poles are disposed adjacent one another and the magnets repel. Accordingly, after magnet 44 is drawn internally by the cable 42 against magnet 46 during the insertion process, by then releasing cable 42, magnet 46 will repel magnet 44 and the resultant movement of magnet 44 will assist in passing the cable 42 along a flat bone such as the pelvis.

Figure 9:
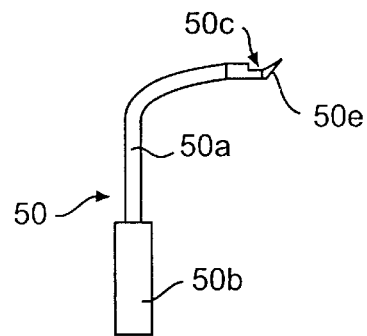
FIG. 9 is a side elevational view of one passer member of a passer device in accordance with yet another embodiment of the invention.
Figure 10:
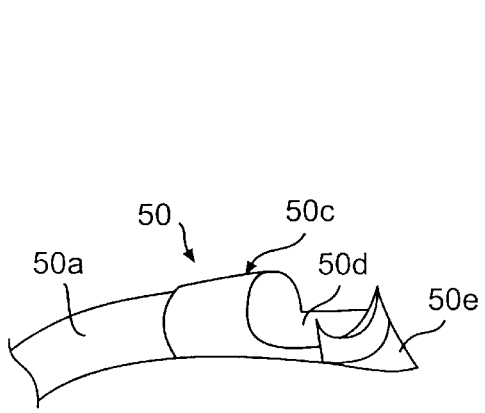
FIG. 10 is a perspective view, drawn to an enlarged scale and partially broken away of a portion of the passer member of FIG. 2.
Figure 11:
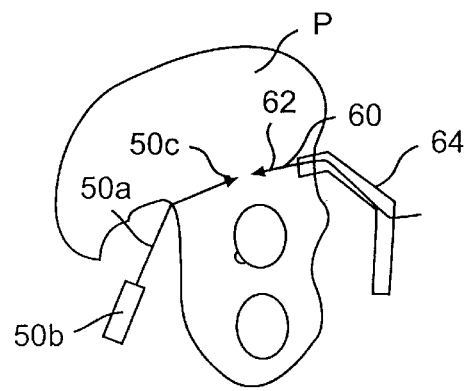
FIG. 11 is a schematic representation of the device of FIG. 9 in use in passing a wire or cable along a pelvic bone.

A further embodiment of the invention is illustrated in FIGS. 9 and 10, and is shown in operation in FIG. 11. This embodiment is intended to be used in combination with a cable having a tip magnet such as that of FIG. 6, and as illustrated in FIG. 6, in this embodiment, a passer device 50 is provided that includes a malleable or bendable rod 50a which is secured to a handle 50b and which further includes a specially shaped distal end portion 50c that provides a mechanical capture. As is best seen in FIG. 10, end portion 50, which is magnetic, includes a recess 50d for receiving a bullet-shaped (or other) magnet as well as a mechanical capture element or prong (or multiple prongs) 50e which is used to draw along a cable-mounted magnet (e.g., corresponding to magnet 44) captured thereby and thus pull along the associated cable or wire secured at the distal end thereof to the magnet. In other words, the mechanical capture element 50e is an extension of magnetic end portion 50c which acts as a "cradle" once the cable-mounted magnet has "jumped" into recess 50d. The capture prong 50e has a "scoop" shape which facilitates insertion of the device, i.e., enables the tip of distal end portion 50c to more easily pass through soft tissue. It will be understood that, in general, although a "scoop" shape is shown, any shape that will perform this function can be employed.

As shown in FIG. 10, wherein a cable 60 with a distal tip magnet 62 is passed by a passer member 64 along a pelvic bone P, the malleable rod 50a enables custom bending thereof into a shape which is adapted as to best capture the magnet 62. It is noted that the malleable rod or wand 50a can be shaped or molded at the time of use so as to provide precisely the right amount of curvature for passage.

It is also noted that shaped or flat magnets mounted on malleable wires, rather than rods, can be used along with the same passers described above.

Although the invention has been described above in relation to preferred embodiments thereof, it will be understood by those skilled in the art that variations and modifications can be effected in these preferred embodiments without departing from the scope and spirit of the invention.

What is claimed is:

1. A surgical passer device for passing a wire or cable around or along a bone of a patient, said passer device comprising:

a first passer member including a first curved cannulated portion having a distal end, including a passage therethrough for receiving a wire or cable to be passed around the bone and having a curvature adapted to fit partially around the bone; and a second passer member including a second curved portion having a distal end and having a curvature adapted to fit partially around the bone such that when, in use of the device, said curved portions of said first and second passer members are brought into engagement with each other at the distal ends thereof the passer device fits around the bone; said second passer member including a permanent magnet at the distal end of said second curved portion for facilitating passing around the bone of a wire or cable exiting from the passage in the cannulated portion of said first passer member.

2. A surgical passer device in accordance with claim 1 wherein said permanent magnet comprises a cannulated magnet and said second curved portion includes a passage therethrough, said first curved portion further including a cannulated permanent magnet at the distal end thereof such that when the cannulated magnets of said first and second portions are engaged, a wire or cable can be passed around the bone through the passages in said first and second curved portions.

3. A surgical passer device in accordance with claim 2 wherein said first and second passer devices respectively comprise first and second handle portions including first and second further magnets, respectively, said first and second magnets being disposed in said handles so as to face each other so that when said further magnets are magnetically engaged, said first and second cannulated magnets are also magnetically engaged.

4. A surgical passer device in accordance with claim 2 wherein said cannulated magnets have slanted distal surfaces.

5. A surgical passer device in accordance with claim 1 wherein the wire or cable to be passed comprises a flexible elongate wire or cable element having a permanent distal magnet at the distal end thereof and said permanent magnet at the distal end of said second curved portion includes means for engaging said distal permanent magnet so as to enable pulling of said flexible elongate element through the passage of said first passer member and around the bone.

6. A surgical passer device in accordance with claim 5 wherein said distal magnet has a non-flat shape and the magnet at the distal end of said second portion has a reciprocal non-flat shape.

7. A surgical passer device in accordance with claim 6 wherein said distal magnet has a bullet shape and said magnet at the distal end of said second portion includes a recessed portion for receiving said distal magnet.

8. A surgical passer device in accordance with claim 7 wherein said distal end of said second portion includes at least one mechanical capture element.

9. A surgical passer device in accordance with claim 8 wherein said mechanical capture element includes a scooped shape for facilitating passage thereof through soft tissue adjacent to the bone.

10. A surgical passer device in accordance with claim 5 wherein said curved second portion of said second passer member comprises a malleable rod bendable to a desired curved shape by the user.

11. A surgical passer device in accordance with claim 5 wherein said first curved portion of said first passer member includes a permanent magnet, at the distal end thereof, of like polarity to that of said distal magnet of said flexible elongate element for repelling said distal magnet upon release of said flexible elongate element.

12. A surgical passer device for passing a wire and cable around and along a bone of a patient, said passer device comprising:
   first and second passer members, said first passer member including a first curved cannulated portion having a first distal end and including a first passage therethrough for passing a wire or cable to said distal end, and a first cannulated magnet at said distal end; and said second passer member including a second curved cannulated portion having a second distal end and including a second passage therethrough for receiving a wire or cable passed from the first passer member and a second cannulated magnet of opposite polarity to said first magnet, at said second distal end for, in operation of the device, magnetically engaging said first magnet when said first and second magnets are brought into proximity such that said first and second curved portions fit around a bone about which a wire or cable is to be passed and so as to bring said first and second passages into alignment to thereby enable passing of a wire or cable around the bone through said first and second passages.

13. A surgical passer device in accordance with claim 12 wherein said first and second passer devices respectively comprise first and second handle portions including first and second further magnets, respectively, said first and second magnets being disposed in said handles so as to face each other so that when said further magnets are magnetically engaged, said first and second cannulated magnets are also magnetically engaged.

14. A surgical passer device in accordance with claim 12 wherein said first and second passer members are mirror images of one another.

15. A surgical passer device in accordance with claim 12 wherein said curved portions are substantially C-shaped and, in use, face in opposite directions.

16. A surgical passer device in accordance with claim 13 wherein said passage through the first curved portion of said first passer member includes an inlet opening at a location between the proximal end of the passage and the distal end of the handle portion.

17. A surgical passer device in accordance with claim 3 wherein said passage through the second curved portion of the second passer member includes an exit opening at a location between the proximal end of the passage and the distal end of the handle portion.

18. A surgical passer device in accordance with claim 12 wherein said cannulated magnets comprise neodymium magnets.

19. A surgical passer device in accordance with claim 12 wherein said cannulated magnet have flat distal surfaces.

20. A surgical passer device in accordance with claim 12 wherein said cannulated magnets have slanted distal surfaces.

21. A surgical passer device in accordance with claim 20 wherein said distal surfaces are oppositely slanted at 45° so as to mate with one another.

22. A surgical passer device for passing a wire or cable around or along a bone of a patient, said passer device comprising:
   a flexible elongate wire or cable element having a distal end and including a distal permanent magnet at said distal end;
   a first passer member including a first curved cannulated portion having a first distal end and including a passage therethrough for receiving the flexible elongate element, with said distal magnet of the flexible elongate element disposed at the distal end of said passage, and having a curvature adapted to fit partially around the bone; and
   a second passer member including a second curved portion having a distal end and having a curvature adapted to fit partially around the bone such that when, in use of the device, said curved first and second curved portions are brought into engagement with each other at the distal ends therein, the passer device fits around the bone; said second passer member including a permanent capture magnet at the distal end of said second curved portion for, in use of the passer device, magnetically engaging said distal magnet so as to enable pulling around the bone of the flexible elongate element through the passage in the cannulated portion of said first member.

23. A surgical passer device in accordance with claim 22 wherein said curved second portion of said second passer member comprises a malleable rod bendable to a desired curved shape by the user.

* * * * *